United States Patent [19]
Miekka et al.

[11] Patent Number: 6,106,773
[45] Date of Patent: Aug. 22, 2000

[54] PATHOGEN INACTIVATING COMPOSITIONS FOR DISINFECTING BIOLOGICAL FLUIDS

[75] Inventors: Shirley I. Miekka, Gaithersburg, Md.; William N. Drohan, Springfield, Va.; Annemarie Ralston, Bethesda; Hao Xue, North Potomac, both of Md.

[73] Assignee: American National Red Cross, Falls Church, Va.

[21] Appl. No.: 09/159,460

[22] Filed: Sep. 24, 1998

[51] Int. Cl.⁷ ...................................................... A61L 9/00
[52] U.S. Cl. ............................ 422/28; 210/633; 210/645; 210/663; 422/29; 422/31
[58] Field of Search .................................. 422/28, 37, 31, 422/29, 663; 210/656, 767, 633, 645

[56] References Cited

U.S. PATENT DOCUMENTS

| | | |
|---|---|---|
| 3,401,005 | 9/1968 | Katz . |
| 3,817,860 | 6/1974 | Lambert et al. . |
| 4,010,259 | 3/1977 | Johansson . |
| 4,076,622 | 2/1978 | Costin . |
| 4,187,183 | 2/1980 | Hatch . |
| 4,238,477 | 12/1980 | Lambert et al. . |
| 4,381,380 | 4/1983 | LeVeen et al. . |
| 4,396,608 | 8/1983 | Tenold . |
| 4,420,590 | 12/1983 | Gartner . |
| 4,460,642 | 7/1984 | Errede . |
| 4,499,073 | 2/1985 | Tenold . |
| 4,594,392 | 6/1986 | Hatch . |
| 4,883,587 | 11/1989 | LeVeen et al. . |
| 4,888,118 | 12/1989 | Barnes et al. . |
| 4,915,839 | 4/1990 | Marinaccio et al. . |
| 4,946,673 | 8/1990 | Pollack . |
| 4,999,190 | 3/1991 | Fina et al. . |
| 5,071,648 | 12/1991 | Rosenblatt . |
| 5,137,718 | 8/1992 | Gillespie . |
| 5,176,836 | 1/1993 | Sauer et al. . |
| 5,302,392 | 4/1994 | Karakelle et al. . |
| 5,326,841 | 7/1994 | Fellman . |
| 5,360,605 | 11/1994 | Shanbrom . |
| 5,370,869 | 12/1994 | Shanbrom . |
| 5,431,908 | 7/1995 | Lund . |
| 5,545,401 | 8/1996 | Shanbrom . |
| 5,589,072 | 12/1996 | Shanbrom . |
| 5,591,350 | 1/1997 | Piechocki et al. . |
| 5,609,864 | 3/1997 | Shanbrom . |
| 5,624,567 | 1/1997 | Colombo . |
| 5,639,452 | 6/1997 | Messier . |
| 5,814,225 | 9/1998 | Shanbrom ............................... 210/656 |

FOREIGN PATENT DOCUMENTS

| | | |
|---|---|---|
| WO85/02422 | of 1985 | WIPO . |
| WO92/04031 | of 1992 | WIPO . |
| WO92/04061 | of 1992 | WIPO . |
| WO93/04678 | of 1993 | WIPO . |
| WO93/04731 | of 1993 | WIPO . |
| WO93/06911 | of 1993 | WIPO . |
| WO93/17693 | of 1993 | WIPO . |
| WO93/21933 | of 1993 | WIPO . |
| WO93/25268 | of 1993 | WIPO . |
| WO94/04730 | of 1993 | WIPO . |
| WO93/00011 | of 1994 | WIPO . |
| WO94/06289 | of 1994 | WIPO . |
| WO97/48422 | of 1997 | WIPO . |
| WO97/48482 | of 1997 | WIPO . |

OTHER PUBLICATIONS

Miekka et al, "Newl Methods for Inactivation of Lipid–Enveloped and Non–Enveloped Viruses", *Haemophilia*, vol. 4, pp. 402–408 (1998).

Gottardi, W., "Iodine and Iodine Compounds in Disinfection, Sterilization, and Preservation", (Block, Seymour S., Ed.) Lea & Febiger, Philadelphia (3d ed., 1983).

L.E. Osterhoudt, "Iodinated resin and its use in water disinfection" *Say You Saw It In Filtration News* May/Jun. 1996 Issue p. 22.

*Primary Examiner*—Krisanne Thornton
*Attorney, Agent, or Firm*—Burns, Doane, Swecker & Mathis, L.L.P.

[57] ABSTRACT

The present invention is directed to pathogen inactivating compositions that can be used to disinfect various biological fluids, such as blood, blood fractions, and the like. The compositions are suitable for disinfecting biological fluids containing valuable, but labile, components such as proteins without destroying the desired properties of such components. The pathogen inactivating compositions of the present invention are produced by contacting water or an aqueous solution with iodinated matrix material. The compositions can be pre-formulated and stored for subsequent use in disinfecting a wide range of biological fluids.

27 Claims, No Drawings

PATHOGEN INACTIVATING COMPOSITIONS FOR DISINFECTING BIOLOGICAL FLUIDS

FIELD OF THE INVENTION

The present invention provides a pathogen inactivating composition (also referred to herein as PIC) that disinfects biological fluids without substantially compromising the biological activity or other desirable properties of proteins or other desirable components within said biological fluids. The pathogen inactivating compositions of the present invention can be produced, for example, by contacting water or an aqueous solution with iodinated ion exchange matrix material. These compositions can be prepared in bulk and stored for subsequent use in inactivating pathogens such as viruses, bacteria, prions, and the like in biological fluids, particularly, blood, blood fractions, and blood products.

BACKGROUND OF THE INVENTION

The use of iodine as an aerial disinfectant has been advocated at least since 1926. Iodine is also known to be useful in disinfecting drinking water. Iodine can inactivate viruses over a wide range of water quality.

Johansson, U.S. Pat. No. 4,010,259, described methods and materials for complexing iodine with various iodophors. The iodophors of the '259 patent are described as those in which the iodine is non-covalently bonded to a hydrophilic organic carrier. The organic carrier is insoluble and may exhibit ion exchange groups in water, but capable of swelling in water to form a gel. U.S. Pat. Nos. 5,360,605 and 5,370,869 represent that iodine complexed with polyvinyl pyrrolidone ("PVP", e.g., povidone USP), is an effective iodophor for killing or inactivating certain pathogens in biological fluids, particularly platelet-bearing fluid.

Disinfection of water by the use of iodine bound to anion exchange resins has been described by Hatch (U.S. Pat. No. 4,594,392; U.S. Pat. No. 4,190,529 and Ind. Eng. Chem. Prod. Res. Dev. 20 (1981) 392–385); and Gartner (U.S. Pat. No. 4,420,590).

It has also been found that certain iodinated matrices can disinfect biological fluids, i.e., fluids containing labile, biologically active components such as proteins, particularly blood derived proteins. Such iodinated matrices are disclosed in U.S. patent application Ser. No. 08/813,337, filed Mar. 7, 1997, (which corresponds to WO 97/48482) which is a continuation in part application of U.S. patent application Ser. No. 08/667,448, filed Jun. 21, 1996 (which corresponds to WO 97/48422) both of which are incorporated herein by reference.

Until recently, it was believed that such matrices required direct contact or substantial proximity with the proteins of the biological fluid. For example, it is known that iodine species complex with amine groups to form iodamines. Gottardi, W., *Iodine and Iodine Compounds in Disinfection, Sterilization, and Preservation,* (Block, Seymour S., Ed.) Lea & Febiger, Philadelphia (3d ed., 1983). Further, such iodamines can be formed by reaction of iodine with the amine residue in proteins. When exposed to proteinaceous fluids, iodinated matrices might create an iodamine reservoir that releases iodine into the fluid over extended periods thereby disinfecting the fluid. Thus, one of skill in the art would expect that such solution phase effects in iodinated matrices are influenced by the presence of protein, and might even be protein-dependent.

Until recently, it was also believed that such iodinated matrices exerted their pathogen inactivation effect only through direct contact with the solution containing the organism to be inactivated. During this time of direct contact, the organism was thought to be inactivated by exposure to the high levels of iodine present on the matrix.

The direct contact method, however, presents potential drawbacks. Generally, proteins are ionic and thus under certain conditions can bind to ionic exchange matrices. If a protein of interest were to bind to an iodinated matrix, it would be subjected to short term exposure to high concentrations of iodine. The ionic composition and pH of the protein solution must be tailored to prevent such binding. This places limits on the solution conditions useful in the direct contact method.

It has now been discovered that non-proteinaceous fluids, such as water and other polar solvents, can extract a pathogen inactivating agent from iodinated ion exchange matrices. The resulting pathogen inactivating composition (or "PIC") contains a water soluble pathogen inactivating agent that can be readily separated from the iodinated matrix material, stored, and subsequently used to disinfect biological fluids. Compared to methods requiring that the biological fluid directly contact the iodinated matrix (see, e.g., WO97 48422 and WO97 48482), PICs provide a more mild and facile means for disinfection. The PICs of the invention are more convenient in application, and reduce the likelihood that proteins will be denatured or otherwise destroyed during disinfection.

OBJECTS AND SUMMARY OF THE INVENTION

It is an object of the present invention to provide materials and methods for disinfecting biological fluids as defined below.

It is an additional object of the present invention to provide a reliable, storage stable, commercially available composition for inactivating pathogens in biological fluids.

It is a further object of the present invention to provide a reliable, storage stable, commercially available material that can disinfect biological fluids without destroying or damaging the biologically and therapeutically significant components therein.

It is a still further objective of the present invention to provide a means for disinfecting biological fluids in a facile manner that does not involve costly or lengthy processing. Thus, it is an objective of this invention to provide a means for disinfecting fluids by merely combining the fluid to be disinfected with a composition containing a pathogen inactivating agent.

These and other objects of the present invention are fulfilled by the methods and materials disclosed herein.

DETAILED DESCRIPTION OF THE PREFERRED EMBODIMENTS

The present invention provides pathogen inactivating compositions for disinfecting biological fluids. The PICs of the present invention are storable and conveniently applied in the disinfection of a variety of biological fluids.

The PICs of the present invention can be created by extracting a discrete active agent from, e.g., the iodinated matrices described hereinbelow. The active agent is a small molecule (i.e., is separable by dialysis and of a molecular size of less than about 6,000 Daltons); it can be both created and extracted from an iodinated matrix material without the presence or participation of proteins (i.e., is not a protein dependant reaction); and successfully disinfects proteinaceous fluids without direct contact of the proteinaceous fluid with the iodinated matrix.

Materials useful in the present invention include insoluble matrix materials complexed with a disinfecting agent such as a halogen, particularly iodine Other halogens or mixed halogens might also be used. Preferred materials include iodinated gel filtration matrices. Particularly preferred matrix materials are iodinated anion exchange resins.

As used herein, and unless stated otherwise, the term "iodine" (or "liodinated") includes iodine in any of its various forms, e.g., diatomic iodine ($I_2$), iodine as free radical, molecular ionic iodine (e.g., triiodide anion ($I_3^-$), and related species derived from $I_2$.

The term "blood products" includes blood fractions and blood extracts such as plasma and blood derived products such as clotting factors, red cell platelets, white cells, immunoglobulins and the like.

The term "biological fluid" refers to a liquid containing one or more components having a desired biological activity, e.g., proteins. A biological fluid might be of human or non-human origin; a solution, mixture or suspension; and includes, among other things, blood, blood fractions, blood extracts, plasma, milk, urine, semen, saliva, plant extracts, reaction products derived from vaccine production, cell culture supernatants, and other fluids, of either natural or synthetic origin (e.g. recombinant or transgenic).

The term "matrix material" refers to any insoluble, durable material conventionally used as a carrier or substrate material in a separation process and capable of complexing, adsorbing, or otherwise binding iodine in a releasable form; and The term "disinfect" means to remove, kill, destroy, or otherwise inactivate a pathogenic component. Likewise, the term "pathogen inactivation" or "pathogen inactivating" means removing, killing, destroying, or otherwise inactivating pathogenic components. Examples of pathogenic components are a virus, bacterium, microorganism, or other pathogenic species such as the infective agent for transmissible spongiform encephalopathies, e.g., prion, prion-related protein ("PRP"), and the like.

Unless stated otherwise, all quantities or concentrations expressed as a percentage (%) are percent by weight.

The present invention affords a means for pre-fabricating a pathogen inactivating composition by directly contacting aqueous solvents, and the like with iodinated gel filtration media, particularly ion exchange matrices. Nonaqueous solvents might also be employed.

Iodinated matrix materials that are useful in creating the pathogen inactivating compositions of the present include those described in PCT Publication Nos. WO97 48482 and WO97 48422. The resulting formulation is a potent pathogen inactivating composition that does not deleteriously affect other biologically active components within the fluid. Thus, the resulting composition can be mixed with biological fluids to achieve disinfection without significant loss of potentially therapeutic properties of proteins and the like.

A variety of matrix materials are useful as iodine carriers. The matrix material might be an organic or inorganic compound, a synthetic resin, a polyhydroxylic material, or other suitable insoluble carrier or support material. Such polyhydroxylic materials include starch; polysaccharides such as dextran, dextrin, cellulose, and agarose; polyvinyl alcohol; polyvinyl acetal; and the like. Also useful are synthetic resins such as polyacrylamide, methacrylate, azlactone, styrene divinyl benzene copolymers, as well as ceramic- or silica-based materials such as controlled-pore glass; and further include solid beads made of plastic material such as polyethylene, polypropylene, polystyrene, and the like.

Polyhydroxylic matrix materials, such as polysaccharides, and synthetic polymers such as polyacrylamide, and mixed polymers thereof, are preferred.

A wide variety of chromatographic matrices or carrier materials, both charged and uncharged, will take up iodine. When an aqueous solution is passed over these iodinated matrices, it extracts an active agent from the iodinated matrices. The aqueous solution effluent, containing the active agent, can then be mixed with biological fluids in need of disinfection.

Methods and materials conventionally employed in, e.g., size exclusion or gel filtration chromatography can be effectively employed in the present invention as the carrier matrix for iodine. A variety of suitable matrices are commercially available (e.g., cross-linked polyacrylamide, cross-linked glucose polymer (dextrans), cross-linked agarose, and mixed polymers thereof). More specifically, matrices useful in the present invention include underivatized and derivatized forms of cross-linked dextrans, e.g., SEPHADEX® G-10, G-25, G-50, or G-75 (Amersham Pharmacia Biotech AB), PDX (Polydex Biologicals, Ltd.); celluloses; cross-linked agarose, e.g. SEPHAROSE CL2B, CL4B, CL6B, 4 FAST FLOW, 6 FAST FLOW, or BIG BEADS (Amersham Pharmacia Biotech AB); BIOGEL® A (BioRad) or agarose-acrylamide mixtures. e.g., SEPHACRYL® S-100, S-200, S-300 or S-400 (Amersham Pharmacia Biotech AB); styrene/divinylbenzene copolymerized resins, e.g., POROS® (PerSeptive Biosystems), Bio-Rex® 5 (BioRad), AG® 1, AG® 2 or MP-1 (BioRad); acrylics, e.g., AG®4-X4 (BioRad); polyamine, e.g., AG® 3-X4 (BioRad); azlactone (EMPHAZE™, 3M); hydrophobic resins for hydrophobic interaction chromatography (HIC), e.g., C2 BIOGEL® (BioRad), octyl agarose 4XL (Affinity Chromatography Limited (ACL)); polystyrene beads or polystyrene latex particles; combinations and copolymers thereof, and other suitable matrix materials.

Especially preferred matrices are those in which the polymer matrix has been derivatized with functional groups to impart ion exchange (cation or anion exchange) capabilities to the resin. Ion exchange resins, in particular anion exchange resins, appear to be more effective in taking up iodine and functioning as iodinated disinfecting agents than unmodified gel filtration resins.

Suitable cationic functional groups (anion exchangers) include primary, secondary, tertiary, and quaternary ammonium groups, such as aminoethyl (AE-derivatized matrices); diethylaminoethyl (DEAE-derivatized matrices) and dimethylaminoethyl (DMAE-derivatized matrices); trimethylaminoethyl (TMAE-derivatized matrices); and diethyl-(2-hydroxypropyl)aminoethyl (QAE-derivatized matrices).

Commercially available cationic anion exchange matrices include: DEAE SEPHADEX (Amersham Pharmacia Biotech AB or "APB," DEAE SEPHACEL (APB), DEAE SEPHAROSE FAST FLOW (APB), DEAE SEPHAROSE CL-6B (APB), DEAE POROS (Perseptive BioSystems), QAE CELLEX (BioRad), QAE SEPHADEX (APB), Q SEPHAROSE FAST FLOW (APB), DEAE BIO-GEL A (BioRad), DEAE Cellulose (Whatman, Pierce), AG & Biorex Styrene/Divinyl Benzene Resins (BioRad), Anion exchange Macro-Prep Supports (BioRad), Fractogel® EMD DEAE, TMAC, or DEAE (E. Merck), TOYOPEARL DEAE (TosoHaas), TOYOPEARL-QAE (TosoHaas), Q HyperD®

(BioSepra), DEAE TRIS ACRYL® (BioSepra), DEAE SPHEROSIL® (BioSepra). A preferred matrix material is DEAE Sepharose Fast flow (DSFF), i.e., an agarose based matrix carrying diethyl amino ethyl groups.

Typical cation exchange resins include resins derivatized with carboxymethyl moieties (CM-derivatized matrices); phospho moieties; and sulphopropyl (SP-derivatized matrices).

Further we have observed that the pathogen inactivating activity, although having a limited lifetime, persists in the column effluent for hours, and to some extent for weeks or months.

The present invention affords a means for creating a solution-based aqueous phase pathogen inactivating composition that can be conveniently mixed with the biological fluid sought to be disinfected. The mixture is maintained for a sufficient period to effect the desired pathogen inactivation. Subsequently, the mixture can be treated in accordance with conventional practices, e.g., dialysis, to remove unwanted agents.

The method of the present invention provides a facile disinfection process that eliminates passage of sensitive, often labile, biological materials through harsh oxidizing environments such as those laden with various forms of iodine. Further, the method of the present invention affords means whereby the pathogen inactivating composition can be pre-formulated in bulk, packaged, and shipped to end users. Thus, the present invention provides a ready to use pathogen inactivating composition that allows end users to avoid bulk processing and related capital intensive equipment.

The present invention further includes a means for creating a pathogen inactivating composition comprising contacting an iodinated ion-exchange resin with water or an aqueous solution. The pathogen inactivating composition is combined with a biological fluid to effect pathogen inactivation. The pathogen inactivating composition of the present invention can be pre-fabricated consistent with the methods disclosed herein below for directly contacting aqueous biological fluids with iodinated resins. That is, water or an aqueous solution (e.g., water mixed with salts, buffers, stabilizers and other suitable excipients or preservatives) is brought into contact with the iodinated resin; but in the case of the present invention such contact is effected in the absence of the biological fluid. Rather, the pathogen inactivating composition and the biological fluid sought to be disinfected are subsequently combined in a separate step.

Preferably, an intermediate step is effected wherein the PIC is exposed to a capture step, as is described more fully below (and in WO97 48482 and WO97 48422). That is, the PIC is brought into contact with a non-iodinated matrix material (e.g., cross-linked dextrans or cross-linked agaroses derivatized to effect ion exchange) prior to contacting the PIC with the biological fluid of interest. The resulting PIC can be subsequently mixed with the desired biological fluid as in the incubation step described below.

The pathogen inactivating agent can later be removed from the biological fluid in accordance with the "removal" steps described herein below and/or in WO97 48482 and WO97 48422, or in accordance with conventional separation or extraction methods as are otherwise known in the art.

Iodination of Media

Various iodination techniques are suitable for iodinating the chromatographic media or insoluble matrix material useful in the present invention. For example, the chromatographic media can be: (i) mixed dry with elemental iodine at a temperature between 0° C. and 100° C.; (ii) exposed to an iodine vapor-containing environment for a suitable period of time; (iii) mixed in liquid suspension with aqueous solutions containing iodine and iodide (e.g., Lugol's solution); (iv) mixed in suspension with a solution of elemental iodine in alcohol (e.g., ethanol) or other organic solvent, or in mixtures of alcohol and water, or mixtures of other organic solvent(s) and water; or (v) mixed in solution with an iodinated material that releases iodine into the solution or transfers it to the recipient material, or releases/transfers combinations of iodine and/or iodide and/or other reactive iodine species (e.g., $I_3^-$) in a form that complexes, adsorbs, or otherwise binds with the insoluble matrix material.

Matrix materials useful in the present invention are iodinated from about 1% to about 70% iodine (by weight based upon dry weight of the iodinated matrix material).
Preferably, the iodinated matrix materials will have an iodine content of about 20–70%, more preferably about 20–50% iodine; and most preferably about 20–35% iodine.

Pathogen Inactivating Composition

The present invention is an improved alternative to the "direct contact" method for disinfecting protein-containing solutions (i.e., where the biological fluid of interest is directly contacted with the iodinated matrix as disclosed in Shanbrom (WO97 48422) and Shanbrom et al. (WO97 48482). The methods of the present invention involve fewer processing steps, and hence are more cost effective. More specifically, the present methods involve simply intermixing the protein-containing solution of interest with a pre-fabricated pathogen inactivating composition. Such pathogen inactivating compositions are fabricated by removing a pathogen inactivating agent from iodinated matrix material by extraction with an liquid solution. The aqueous solution might contain buffers or salts to facilitate subsequent disinfection of the protein-containing liquid of interest.

A method of utilizing the pre-fabricated pathogen inactivating compositions of the present invention includes an initial aqueous extraction or contact step. That is, a pathogen inactivating composition is first formed by contacting an aqueous liquid of appropriate constitution (e.g., pH, ionic strength, polarity, etc.) with iodinated matrix material; the resulting pathogen inactivating composition is then brought into contact with the biological fluid to be disinfected and properly mixed and/or incubated.

Optionally, a step of iodine capture is effected intermediate the two foregoing steps. Subsequent removal of the pathogen inactivating component, as that term is used herein, produces disinfected biological fluid suitable for subsequent processing or therapeutic use.

Capture refers to an immediate, often in-line, process wherein the aqueous effluent from the iodinated matrices is separated from free iodine remaining in the aqueous solution. Generally, such species are removed from the effluent shortly after collection from the column. Capture can be accomplished by passing the treated solution through, e.g., a non-iodinated anion exchange resin, a polyvinyl acetal ("PVA") filter, or other suitable means for achieving high surface area contact with iodine-binding materials.

A preferred method for creating the PIC and effecting iodine capture involves two columns in series: the first column is packed with the iodinated matrix material; and the second column is packed with a non-iodinated iodine absorbing material, such as an anion exchange resin. As the aqueous solution is passed through the iodinated matrix material, high surface area contact with iodine is achieved; and as the aqueous solution proceeds through the second column, high surface area contact with an iodine absorbing material is achieved.

Further elimination of residual iodine is optionally effected by the addition of reducing agents such as ascorbic acid, reducing sugars, sodium sulfite, glutathione, or other suitable antioxidants following contact of the biological fluid with the iodinated matrix material.

Removal, on the other hand, refers to the removal of the remaining pathogen inactivating species and any undesired iodine-associated reaction products following completion of the disinfecting, or incubation, process. Removal thus refers to a clean-up step that separates the treated protein from the pathogen inactivating agent and undesired reaction by-products and residue.

Removal can be accomplished by separation processes based upon charge, size, or binding affinity. For example, removal can be effected by contacting the PIC-treated biological fluid with an iodine-binding material to remove iodine from the fluid; alternatively, removal can be effected by isolating or separating the protein(s) of interest from the biological fluid, as by binding the proteins to an ion exchange resin.

Preferred methods for achieving removal include any of the following steps: (i) contacting the treated biological fluid with a non-iodinated anion exchange resin to remove iodine, iodide and other reaction products from the protein; (ii) contacting the treated biological fluid with polyvinyl acetal, cross-linked povidone (XLPVP), starch, or other iodine-binding polymer; (iii) diafiltering or ultrafiltering or dialyzing the treated biological fluid to remove iodine and other reaction products; (iv) gel filtering the treated biological fluid to separate the low molecular weight iodine and other reaction products from the higher molecular weight protein; (v) contacting the treated biological fluid with a protein-binding material to bind the protein and permit removal of the pathogen inactivating agent and any other iodine related products and from the treated protein; and/or (vi) contacting the treated biological fluid with an ion-exchange resin to bind the protein and permit removal of the iodine from the treated fluid.

The methods of the present invention thus include a method for formulating a pathogen inactivating composition comprising: (i) contacting a fluid such as water or an aqueous solution with a matrix material iodinated to levels of from about 1% to about 70% iodine (by weight), (ii) removing said solvent or solution from contact with said matrix material, and (iii) capturing and/or reducing residual free iodine in said fluid.

Such pathogen inactivating compositions can be combined with biological fluids to produce the desired pathogen inactivating effect. In one embodiment, a mixture is created of said pathogen inactivating composition and a biological fluid sought to be disinfected, and maintaining said mixture at 0° C. to 60° C. for a period ranging from 10 seconds to 60 days, effecting a removal step, and, optionally, isolating and purifying the protein of interest.

Purification and Disinfection of Biological Fluids

A number of proteins and protein-containing solutions can be disinfected with the materials and methods of the present invention. For example, the materials and methods of the present invention can be used to disinfect biological fluids of the type defined above. Biological fluids of particular interest are those containing albumin; proteases; protease inhibitors; clotting factors such as Fibrinogen, Factor VII, Factor VIII, and Factor IX; protein C; and immunoglobulins, particularly IgG, including hyperimmune Igs, and monoclonal antibodies.

The methods of the present invention are, in some instances, improved by stabilizing the protein or proteins of interest by adding conventional protein stabilizing additives or preservatives to the biological fluid. Those additives include: metal ions or salts such as calcium, magnesium, and manganese; heparin; ethylene diamine tetraacetic acid (EDTA); sucrose and other sugars; cysteine; lysine; glycine; glutathione; and conventional antioxidants.

A preferred embodiment of the present invention involves combining the PICs of the present invention with immunoglobulin solutions, particularly immunoglobulin G solutions (IgG), e.g., Immune Serum Globulin, Immune Globulin, Intravenous Immunoglobulin, and Hyperimmune Globulins.

The preferred temperature for treating immunoglobulin solutions with PIC is about 0° C. to 60° C. A more preferred temperature for treating immunoglobulin solutions with PIC is about 4° C. to 40° C. The most preferred temperature for treating immunoglobulin solutions with PIC is about 20° C. to 37° C.

EXAMPLES

Example 1

PIC Possesses a Small Molecule Active Agent

Two g of 40% iodinated DEAE Sephadex (Iodine/SEPHADEX) was hydrated for 5–10 min in deionized water, and poured into a 1-cm diameter glass chromatographic column to give a packed bed of approximately 7 mL. Two g of non-iodinated DEAE SEPHADEX A25 was hydrated for 2 hours in 1M sodium chloride solution, washed in a suction funnel with 60 mL deionized water and poured into a 1-cm diameter column to give about 12 mL of packed bed. The columns were left at room temperature overnight and were rinsed with additional water to further remove dissolved iodine and salts. The columns were connected in series, with the outlet at the bottom of one Iodine/SEPHADEX column connected by fine-bore tubing to the inlet at the top of the capture column. IgG solution (500 mL, 5% intravenous immunoglobulin solution prepared by Baxter Healthcare in Lessines Belgium) was dialyzed against several changes of deionized water at 4° C. and adjusted to pH 5.5. Deionized water (100 mL) was pumped through the columns at 4 mL/min and the water effluent pool was collected. Then IgG (500 mL) was pumped through the columns and the IgG effluent pool was collected. A 50 mL sample of each pool was dialyzed in SPECTRAPOR tubing (6000–8000 MW cutoff) against four changes of deionized water for 24 hours at 4–6° C. After dialysis was complete, samples of each dialyzed and non dialyzed sample were spiked 1:100 with porcine parvovirus (PPV) stock to give viral titers of $10^{6.6}$ TCID$_{50}$/ML (6.6 log$_{10}$) and incubated for 0, 4, and 24 hours at 37° C. For hold controls, untreated water or IgG, pH adjusted to match the treated samples, were spiked with PPV and incubated. The non-dialyzed water and IgG (IVIG) effluent pools gave similar PPV inactivation rates of 0.65 and 0.75 logs/hour, respectively, both reaching the assay limit by 24 hours. The dialyzed water and IVIG effluent pool samples did not inactivate PPV: the rates of 0.05 and 0.02 log/hour were not different from the slopes of the hold controls (not shown).

This Example demonstrates that the active agent in the PIC of the present invention is (i) a small molecule of less than about 6000 Daltons; (ii) is capable of being created without the participation of proteins; and (iii) is capable of being extracted from iodinated matrices without the participation of proteins. Further, this Example shows that the pathogens need not come into contact with iodinated matrices to be inactivated. Thus, it is possible to disinfect protein-containing biological fluids without the costly and time consuming step of direct contact of the fluid with an iodinated matrix material.

Example 2
Stability of PIC

Two sets of columns containing 2 g of 40% Iodine/SEPHADEX and 2 g of DEAE SEPHADEX A25 were prepared as described above. Cohn Fraction II, an intermediate fraction (≧95% pure) in the purification of IgG, was diafiltered against water and adjusted to pH 5.2. Fraction II (500 mL) was pumped through one set of columns and water (500 mL) was pumped through the other set. The effluent pools were collected and were adjusted to pH 4.1–4.2. Four 30-mL portions of each pool were stored at 37° C., 22° C., 4° C. and −70° C. Samples were removed at intervals, spiked 1:100 with PPV, incubated for 0, 4 and 24 hours at 37° C., and residual viral titers were determined by $TCID_{50}$ assay. Hold controls were untreated, pH-adjusted starting Fraction II or water, stored at 37° C., 22° C., 4° C. and −70° C. alongside the effluent samples. The results showed that there was no detectable loss in virucidal potency up to 55 days at 4° C. in either water or Fraction II. At 22° C., the activity is maintained in water, but not in Fraction II. At 37° C. the activity was gone by 34 days in water and by 14 days in Fraction II. No loss of activity was detected at −70° C. The good stability in aqueous solution at 4° C. demonstrates that column effluent can be prepared, stored, and used later for inactivating viruses in plasma products.

Example 3
pH Dependence of PIC

Two g of 35% Iodine/SEPHADEX was swelled in 50 mL water for 1 hr, packed into a 1 cm diameter column and washed with 5 column volumes of water. Two g of DEAE SEPHADEX A25 was swelled in 50 mL of 0.05 M sodium phosphate, 1 M sodium chloride for 1 hr, washed with water in a suction funnel until the conductivity was below 0.4 mMHO, packed into a 1 cm diameter column and washed with 2 column volumes of water. The columns were connected in series as described above. A pH 5.5 buffer of 0.05 M sodium acetate, 0.05 M sodium phosphate (200 mL) was pumped through the columns. The pool was divided into 4 aliquots. They were adjusted to pH 4.0, 6.0, 8.0 and 10.0 and volume made equal by addition of water. PPV was spiked into each, and the samples were incubated for 0, 1, 2.5 and 4 hours. PPV titers were determined by $TCID_{50}$ assay. The viral inactivation rates were similar at all pH values (ca. 0.75 log/hr). No PPV inactivation was seen in hold controls (untreated acetate/phosphate buffer at pH 4.0, 6.0, 8.0 and 10.0, spiked with PPV and incubated 0 and 4 hours).

Example 4
PIC Inactivates the Infective Agent of Scrapie, a Transmissible Spongiform Encephalopathy Two gram portions of 35% Iodine/Sephadex and DEAE Sephadex A25 were swelled, poured, rinsed and assembled as described in Example 1. Cohn Fraction II (5% protein concentration, diafiltered against water, was adjusted to pH 5.5 and a sample was removed as untreated control. The protein solution (510 mL) was pumped through the two columns at 2–4 mL/min, the first 10 mL hold-up volume being discharged and the remaining 500 mL collected. The effluent pool was adjusted to pH 4.5 and was stirred well to assure pool homogeneity. Samples of the untreated control (10 mL) and the effluent pool (110 mL) were transported to the scrapie testing facility, where they were spiked 1:10 with a 10% homogenate of scrapie-infected hamster brain and incubated for 0 or 72 hours at 37° C. Ten-fold serial dilutions of the samples were prepared and inoculated intracerebrally into hamsters (four to eight animals per dilution). The animals were monitored for signs of scrapie disease for several months. The infective titers as of 230 days post inoculation are shown in the following table:

| Sample | Scrapie Titer ($Log_{10}$) | Reduction Factor ($Log_{10}$) |
|---|---|---|
| Spiked Fr. II (Unincubated control) | 8.75 | — |
| Iodine/Sephadex effluent, spiked and incubated 72 hr at 37° C. | 6.25–6.75 | 2.0–2.5 |

At the same time that scrapie was spiked into the Iodine/Sephadex column effluent, aliquots if the tested sample were spiked with porcine parvovirus and incubated 2, 4 and 18 hours at 37° C. The rate of inactivation for parvovirus averaged 0.75 log/hr. The rate of inactivation of scrapie averaged 0.028–0.035 log/hr over the 72 hours incubation period.

Example 5
PIC Inactivation of PPV With Various Plasma Proteins

One g portions of 35% Iodine/SEPHADEX and non-iodinated DEAE SEPHADEX A25 were hydrated as described above and packed into 1-cm diameter glass columns. Water (250 mL) was pumped through the two columns at a flow rate of 1 mL/min. The 250 mL effluent pool was collected and used to inactivate viruses in plasma proteins as described below.

A. Treatment of Coagulation Factor VIII (CFVIII):

Human Anti-hemophilic Factor, Method M, Solvent/Detergent Treated (American Red Cross, Lot 29359030AA) was reconstituted in water according to package directions, and was then dialyzed against several changes of water and adjusted to pH 5.5. Two mL of the dialyzed CFVIII was mixed with 2 mL of column effluent (1-to-1 ratio) or with 0.2 mL of column effluent (1-to-10 ratio). The mixtures were spiked with PPV to give a titer of 7.4 $log_{10}$ $TCID_{50}$/mL, and were incubated at 37° C. for 2, 4 and 24 hours. A hold control of PPV spiked into the CFVIII solution was incubated under the same conditions. In the 1-to-1 sample, the PPV titer decreased to 2.88 log at 24 hours (4.55 $log_{10}$ decrease; average rate 0.19 $log_{10}$/hr). In the 1-to-10 sample, the PPV titer decreased to 7.25 log in 24 hours (0.18 $log_{10}$ decrease) which was similar to the hold control. When incubated with column effluent under similar conditions without virus, 70–90% of the original Factor VIII clotting activity was maintained.

B. Treatment of Coagulation Factor IX(CFIX):

Human Coagulation Factor IX, Solvent/Detergent Treated (American Red Cross, Lot 28309124A) was reconstituted and dialyzed extensively against water. Two mL of dialyzed CFIX was mixed with 2 mL of column effluent (1-to-1 ratio) or 0.2 mL of column effluent (1-to-10 ratio). Hold controls were prepared and the mixtures were spiked with PPV and incubated at 37° C. as described for CFVIII. In the 1-to-1 sample the virus titer decreased to 2 $log_{10}$ at 24 hours (5.43 $log_{10}$ decrease, average rate 0.23 $log_{10}$/hr). In the 1-to-10 mixture and the hold control, the virus titer decreased to 6.55 $log_{10}$ (0.88 $log_{10}$ decrease, average rate 0.04 log/hr).

C. Treatment of Albumin:

Human albumin, 25% solution (Baxter Healthcare, Lot 28376261AB) was dialyzed against water and adjusted to pH 5.5. Two mL of the prepared albumin was mixed with 2 mL of column effluent (1-to-1 ratio) or with 8 mL of column effluent (4-to-1 ratio), spiked with PPV and incubated at 37° C. alongside spiked controls. The PPV titer in the 4-to-1 sample decreased to 2.53 log at 24 hours (4.9 $\log_{10}$ average rate 0.20 log/hr). In the 1-to-1 sample, the PPV titer reached 6.2 log (1.2 $\log_{10}$ decrease, rate 0.05 $\log_{10}$/hr) which was only slightly more than the hold control at 6.55 log (0.04 log/hr).

D. Treatment of Plasma:

A single unit of human fresh frozen plasma (blood group O+) was thawed, dialyzed against water and adjusted to pH 5.5. It was then mixed with the column effluent to prepare 1-to-1 and 4-to-1 mixtures, spiked with PPV and incubated as described for albumin. In 24 hours, the PPV titer in the 4-to-1 mixture decreased to ≦1.13 log (≧6.3 $log_{10}$ reduction, or ≧0.26 $log_{10}$/hr), and the 1-to-1 mixture decreased to 4.98 log (2.5 $log_{10}$ reduction, or 0.10 log/hr)

Example 6

PIC Inactivation of PPV in Presence of API

Alpha-1-proteinase inhibitor (API) was purified from human plasma. Two gram portions of 40% Iodine/SEPHADEX and DEAE SEPHADEX A25 were swelled, packed and washed as described above. Water (200 mL) was pumped through the two columns at a flow rate of 4 mL/min. The 200 mL effluent pool was collected. An aliquot of the pool was evaluated for PPV inactivation in the presence and absence of API, and for its effect on elastase inhibitory activity of API. Column effluent was mixed 1:1 with API solution or with sterile saline and spiked with PPV. Incubation for 24 hrs. at 37° C. brought about complete inactivation of PPV in both samples. When column effluent was mixed 1:1 with API and incubated without virus, the API activity after 24 hours of incubation was 94.5% of the starting activity.

For yet another example of pathogen inactivation in the presence of API, see copending U.S. patent application Ser. No. 09/159,461 filed, Sep. 24, 1998, entitled "Method for Purification of Alpha-1 Proteinase Inhibitor", which is incorporated herein by reference.

The foregoing examples are merely illustrative of the present invention; variation and optimization of the methods and materials of the present invention may be effected as applied to the disinfection of other products and materials, and are within the skill of one of ordinary skill in the art.

What is claimed is:

1. A non-matrix-associated pathogen inactivating composition for disinfecting biological fluids produced by a process comprising an aqueous extraction of a soluble pathogen inactivating agent from an iodinated matrix material and separating said agent from residual free iodine.

2. The pathogen inactivating composition of claim 1, wherein iodine has been removed from said composition by a step of iodine capture.

3. The pathogen inactivating composition of claim 1, wherein said iodinated matrix material is an iodinated anion exchange resin.

4. The pathogen inactivating composition of claim 1, wherein said matrix material is derivatized to possess a cationic functional group and is formed of a material selected from the group consisting of; a dextran, an agarose, a cellulose, a synthetic polymer, and mixtures thereof.

5. The pathogen inactivating composition of claim 4, wherein said cationic functional group is selected from the group consisting of diethylaminoethyl, aminoethyl, diethyl-(2-hydroxypropyl)aminoethyl, dimethylaminoethyl, trimethyl aminoethyl, trimethyl aminomethyl, and triethyl aminoethyl.

6. The pathogen inactivating composition of claim 4, wherein said matrix material is complexed with about 1–70% (by weight) iodine.

7. The pathogen inactivating composition of claim 1, wherein said iodinated matrix material is a DEAE-derivatized cross-linked dextran matrix material iodinated to levels from about 1% to about 70% iodine (by weight).

8. A method for disinfecting a biological fluid comprising contacting said biological fluid with the pathogen inactivating composition of claim 1.

9. The method of claim 8, wherein said contact comprises mixing said composition with said biological fluid for a period of about 10 seconds to about 60 days at about 0° C. to about 60° C.

10. The method of claim 8, wherein said contact comprises mixing said composition with said biological fluid for a period of about 4 hours to about 48 hours at about 4° C. to about 40° C.

11. The method of claim 8, wherein said method further comprises a step of effecting removal following contacting of said pathogen inactivating composition with said biological fluid.

12. A method for disinfecting a biological fluid comprising:

(a) formulating a pathogen inactivating composition by
  (i) contacting an aqueous liquid with a matrix material iodinated to levels of about 1% to about 70% iodine (by weight),
  (ii) removing said liquid from contact with said matrix material, and
  (iii) effecting iodine capture on said liquid, thereby formulating a non-matrix-associated pathogen inactivating composition; and (b) contacting said pathogen inactivating composition with a biological fluid for a period of about 10 seconds to about 60 days at a temperature of about 0° C. to 60° C. to obtain a disinfected biological fluid;

(c) effecting removal of the pathogen inactivating composition and reaction by-products from the disinfected biological fluid of step (b).

13. A method for disinfecting a biological fluid comprising:

(a) formulating a pathogen inactivating composition by
  (i) contacting an aqueous liquid having a pH of between 5.0 and 6.5 and an ionic strength of between about 0 and about 1.0 with a matrix material iodinated to levels of about 20% to about 50% iodine (by weight),
  (ii) removing said liquid from contact with said matrix material, and
  (iii) effecting iodine capture on said liquid, thereby formulating a non-matrix-associated pathogen inactivating composition;

(b) contacting said pathogen inactivating composition with a biological fluid for a period of about 4 hours to about 48 hours at a temperature of about 4° C. to 40° C. to obtain a disinfected biological fluid;

(c) effecting removal of the pathogen inactivating composition and reaction by-products from the disinfected biological fluid of step (b).

14. A method for disinfecting a biological fluid comprising:

(a) formulating a pathogen inactivating composition by
  (i) contacting an aqueous liquid having a pH of about 5.5 with a matrix material iodinated to levels of about 20% to about 50% iodine (by weight),
  (ii) removing said liquid from contact with said matrix material, and
  (iii) effecting iodine capture on said liquid, thereby formulating a non-matrix-associated pathogen inactivating composition;

(b) contacting said pathogen inactivating composition with a biological fluid for a period of about 4 hours to about 48 hours at a temperature of about 37° C. to obtain a disinfected biological fluid;

(c) effecting removal of the pathogen inactivating composition and reaction by-products from the disinfected biological fluid of step (b).

15. A method for producing a non-matrix-associated pathogen inactivating composition comprising contacting an aqueous liquid with an iodinated matrix material, thereby producing a non-matrix-associated pathogen inactivating composition.

16. The method of claim 15, wherein said process further comprises a step of effecting iodine capture.

17. The method of claim 15, wherein said iodinated matrix material is an iodinated anion exchange resin.

18. The method of claim 15, wherein said matrix material is derivatized to possess a cationic functional group and is formed of a material selected from the group consisting of: a dextran, an agarose, a cellulose, and mixtures thereof.

19. The method of claim 15, wherein said cationic functional group is selected from the group consisting of diethylaminoethyl, aminoethyl, diethyl-(2-hydroxypropyl)aminoethyl, dimethylaminoethyl, trimethyl aminoethyl trimethyl aminomethyl and triethyl aminoethyl.

20. The method of claim 15, wherein said matrix material is complexed with about 1 to about 70% (by weight) iodine.

21. The method of claim 15, wherein said iodinated matrix material is a DEAE-derivatized cross-linked dextran matrix material iodinated to levels from about 1% to about 70% iodine (by weight).

22. A method for forming a non-matrix-associated pathogen inactivating composition comprising:

(i) contacting an aqueous solution having a pH of about 5.0 to about 6.5 with a dextran matrix material iodinated to levels of about 20% to about 50% iodine (by weight);

(ii) removing said solution from contact with said matrix material; and (iii) effecting iodine capture, thereby forming a non-matrix-associated pathogen inactivating composition.

23. The method of claim 22, wherein said dextran matrix material is derivatized with a cationic functional group selected from the group consisting of diethylaminoethyl, aminoethyl, diethyl-(2-hydroxypropyl)aminoethyl, dimethylaminoethyl, trimethyl aminoethyl, trimethyl aminomethyl, and triethyl aminoethyl.

24. A method for forming a non-matrix-associated pathogen inactivating composition comprising:

(i) contacting an aqueous solution having a pH of about 5.0 to about 6.5 with an agarose matrix material iodinated to levels of about 20% to about 50% iodine (by weight), (ii) removing said solution from contact with said matrix material, and (iii) effecting iodine capture, thereby formulating a non-matrix-associated pathogen inactivating composition.

25. The method of claim 24, wherein said agarose matrix material is derivatized with a cationic functional group selected from the group consisting of diethylaminoethyl, aminoethyl, diethyl-(2-hydroxypropyl)aminoethyl, dimethylaminoethyl, trimethyl aminoethyl, trimethyl aminomethyl, and triethyl aminoethyl.

26. A storage stable non-matrix-associated pathogen inactivating composition for disinfecting biological fluids produced by a process comprising extracting a pathogen inactivating agent from an iodinated matrix material with an aqueous solvent, removing residual iodine with a step of iodine capture, and storing said composition for subsequent disinfection of a biological fluid.

27. A method for disinfecting a biological fluid comprising mixing a biological fluid with a storage stable pathogen inactivating composition of claim 26 for a period of about 10 seconds to about 60 days at a temperature of about 0° C. to 60° C., and performing removal on the mixture of said biological fluid and said pathogen inactivating composition to obtain a disinfected biological fluid.

* * * * *